United States Patent
Brucksch et al.

(10) Patent No.: US 7,493,824 B2
(45) Date of Patent: Feb. 24, 2009

(54) CONNECTING ELEMENT FOR THE RELEASABLE SEALED CONNECTION OF A FLUID LINE SYSTEM TO A PRESSURE TRANSDUCER, AND PRESSURE TRANSDUCER FOR IT

(75) Inventors: Ulrich Brucksch, Isernhagen (DE); Rainer Hartwig, Hambuhren (DE)

(73) Assignee: Nikkiso Medical Systems GmbH, Hannover (DE)

( * ) Notice: Subject to any disclaimer, the term of this patent is extended or adjusted under 35 U.S.C. 154(b) by 0 days.

(21) Appl. No.: 11/695,134

(22) Filed: Apr. 2, 2007

(65) Prior Publication Data
US 2007/0234817 A1    Oct. 11, 2007

(30) Foreign Application Priority Data
Apr. 7, 2006    (DE) .................. 10 2006 016 846

(51) Int. Cl.
    *G01L 7/00*    (2006.01)
(52) U.S. Cl. ...................................... 73/756
(58) Field of Classification Search ............. 73/700, 73/706, 747; 600/488
    See application file for complete search history.

(56) References Cited

U.S. PATENT DOCUMENTS 3,721,127 A * 3/1973 Garcea ................... 73/715
4,562,409 A * 12/1985 Saito et al. .............. 330/286
4,562,845 A *  1/1986 Furst et al. .............. 600/488
4,920,972 A *  5/1990 Frank et al. ............. 600/488
5,551,300 A *  9/1996 Vurek et al. ............. 73/706

FOREIGN PATENT DOCUMENTS

| DE | 10032616 | 1/2002 |
| EP | 0685721 | 4/2000 |
| GB | 2029579 | 3/1980 |
| WO | WO98/47424 | 10/1998 |

\* cited by examiner

*Primary Examiner*—Andre J Allen
(74) *Attorney, Agent, or Firm*—Whitham Curtis Christofferson & Cook, PC

(57) ABSTRACT

A connecting element for the releasable sealed connection of a fluid line system to a pressure transducer for detecting positive and negative pressures of a fluid located in the connecting element includes a housing, at least one fluid line connection, and a measuring chamber in the housing. The measuring chamber communicates with the fluid line connection, a diaphragm adjacent to the measuring chamber which is tightly connected to the housing for sealing the measuring chamber, and a connecting section on the housing. The connecting section being a repeatedly releasable connection of the connecting element to the pressure transducer. The connecting section has a tubular connection pointing away from the housing and having at least one locking element.

17 Claims, 2 Drawing Sheets

CONNECTING ELEMENT FOR THE RELEASABLE SEALED CONNECTION OF A FLUID LINE SYSTEM TO A PRESSURE TRANSDUCER, AND PRESSURE TRANSDUCER FOR IT

FIELD OF THE INVENTION

The invention relates to a connecting element for the releasable sealed connection of a fluid line system to a pressure transducer for detecting positive and negative pressures of a fluid located in the connecting element, comprising a housing, at least one fluid line connection to the housing, a measuring chamber in the housing, which measuring chamber communicates with the fluid line connection, a diaphragm adjacent to the measuring chamber, which diaphragm is tightly connected to the housing for sealing the measuring chamber, and a connecting section on the housing for the repeatedly releasable connection of the connecting element to a pressure transducer.

The invention also relates to a pressure transducer for measuring the pressure of a measuring chamber, closed off with a diaphragm, of a separate connecting element which can be connected to the pressure transducer in a releasable and sealed manner, the pressure transducer having a pressure transducer housing, a pressure sensor in the pressure transducer housing and a connecting region, for the repeatedly releasable fastening of the connecting element to the pressure transducer housing, in such a way that the connecting element is connected to the pressure transducer in an airtight manner and there is an air volume, sealed off relative to the atmosphere, between the diaphragm and the pressure sensor, such that a pressure of the diaphragm acts via the air volume on the pressure sensor.

BACKGROUND

For example in dialysis or hemodialysis there is a need to continuously measure and monitor the blood pressure in a line. In this case, for hygienic reasons and for isolating the measuring electronics from the patient, the fluid medium located in a measuring chamber of a separate connecting element is separated from the pressure transducer by a diaphragm. The connecting element is coupled to a fluid line system of a dialysis or hemodialysis apparatus.

Such connecting elements (system elements) and pressure transducers of the generic type are known, for example, from DE 100 32 616 A1. The system element is in this case mounted with spring hooks onto the pressure transducer in such a way that the diaphragm of the system element rests flush and in an airtight manner on a transducer diaphragm of a pressure sensor. The spring hooks engage in the process in an encircling groove at the outer circumference of the housing.

Furthermore, EP 0 685 721 B1 discloses a device for measuring the pressure of a fluid medium, in which device the diaphragm of the system element is pressed onto the transducer diaphragm of the pressure sensor.

SUMMARY

The measurement of the positive or negative fluid pressure requires absolutely tight and precise fastening of the connecting element to the pressure transducer. The pressure measurement during the dialysis or hemodialysis process is critical from the safety point of view, and therefore absolutely reliable seating of the connecting element on the pressure transducer has to be ensured with the simplest operation.

The object of the present invention is therefore to provide an improved connecting element for the releasable sealed connection of a fluid line system to a pressure transducer and to provide an improved pressure transducer for it, said connecting element and said pressure transducer ensuring firm and reliable seating on one another with the simplest operation.

The object is achieved with the connecting element of the type mentioned at the beginning in that the connecting section has a tubular connection, pointing away from the housing and intended for slipping onto or into a corresponding connecting tube of the pressure transducer, and at least one locking element for the repeatedly releasable connection of the connecting element to the pressure transducer, the tubular connection communicating with the diaphragm and being designed for the airtight connection of the connecting element to the pressure transducer.

In contrast to the conventional connecting elements and pressure transducers resting flat one on top of the other, it is proposed with the present invention to connect the connecting element and the pressure transducer to one another by means of corresponding tubular connecting sections engaging one inside the other. In this case, the connecting tubes firstly serve for the reliable and tight fixing of connecting element and pressure transducer on one another. Secondly, the inner connecting tube defines the air volume between diaphragm and pressure sensor of the pressure transducer. The precision of connecting element and pressure transducer is thus substantially determined by the production of the connecting tube defining the air volume and does not depend on the operation.

Owing to the fact that the diaphragm is covered on the outside essentially by the connecting section and is accessible on the outside only via the tubular connection, damage to the diaphragm during the handling of the connecting element is avoided. In addition, the diaphragm is stabilized in such a way that a space in the diaphragm at normal system pressures is reliably avoided in contrast to the conventional free diaphragms.

Due to handling errors, the problem of damage to or of bursting of the diaphragm has often occurred with the conventional exposed diaphragms, as a result of which blood escapes outward from the connecting lines and contaminates the environment and possibly puts the patient at risk.

The locking element is preferably designed as a screw cap with screw thread. In contrast to the conventional snap locks susceptible to faults, such a screw cap can be realized on account of the tubular connecting tubes which engage one inside the other. With the screw cap, a reliable and tight connection of connecting element and pressure transducer can be created by the simplest rapid operation. It is especially advantageous if the screw cap used is a Luer-lock connection, as is normal in hospitals. The operation of such a Luer-lock connection is well known on account of the widespread use in hospitals. In addition, on account of the relatively large thread pitch, the Luer-lock connection offers the advantage that only a small turn is required in order to screw up and release the connecting section.

Optionally, fastening of the connecting element to the pressure transducer rapidly and in the simplest manner by means of a bayonet catch is also conceivable. The bayonet catch may be formed by the tubular connection having a longitudinal slot extending from the free end in the direction of diaphragm and a transverse slot projecting at right angles from the end of the longitudinal slot. A button-like prominence on the corresponding connecting tube of the pressure transducer is then directed into a corresponding longitudinal slot and rotated into the latter when the transverse slot is reached.

Alternatively, the tubular connection of the connecting element may have at least one button-like prominence for inserting into a bayonet catch slot of the pressure transducer. A combination is also conceivable, the tubular connection of the connecting element having a longitudinal slot and a button-like prominence corresponding to a longitudinal slot and to a button-like prominence of the connecting tube of the pressure transducer.

The operation of the locking element can be facilitated in that a sleeve part is provided which is rotatable relative to the tubular connection and has a lever which projects away from the sleeve part and is intended for locking the connecting element on a pressure transducer. Rapid and simple locking can be effected by means of the lever. At the same time, due to the extension direction of the lever, the lock clearly shows whether or not the connecting element is firmly locked to the pressure transducer.

Furthermore, it is advantageous if a hollow is provided in the housing adjacent to the diaphragm and diametrically opposite the measuring chamber. Due to the hollow, the diaphragm can move downward to an even greater extent in the direction of the tubular connection than is possible through the opening in the tubular connection itself. As a result, the measurement of positive pressures in the measuring chamber is improved.

The connecting section is preferably formed integrally with the housing of the connecting element in such a way that said connecting section is mounted onto the housing in a position directly adjacent to the diaphragm and is connected to the housing in an airtight manner in such a way that air pressure is transmitted exclusively from the diaphragm via the tubular connection to a pressure transducer suitable for connection. In this way, the housing diaphragm and the connecting section form a self-contained sealing unit.

To seal the measuring chamber and the air volume between diaphragm and pressure transducer, it is advantageous if the diaphragm has an encircling sealing ring on one side and in an especially preferred manner a respective encircling sealing ring on both sides, and if the housing and the connecting section have encircling grooves for accommodating corresponding sealing rings of the diaphragm.

In this way, an airtight and fluid-tight connection between the housing, the diaphragm and the connection section is achieved. The sealing rings may be formed integrally with the diaphragm by thickened material portions for forming O-rings being produced during manufacture.

The housing, the diaphragm and the connecting section may be adhesively bonded or welded to one another in order to provide an airtight and fluid-tight unit.

The object is also achieved with the pressure transducer of the type mentioned at the beginning in that the connecting region is a connecting tube for accommodating the tubular connection of the connecting element and has locking elements for the repeatedly releasable connection of the tubular connection of the connecting element to the connecting region.

Corresponding to the connecting element, a tubular connection is also provided at the pressure transducer, said tubular connection ensuring a simple, reliable and tight connection of the pressure transducer to the connecting element.

Advantageous embodiments are described in the sub-claims.

DESCRIPTION OF THE DRAWINGS

The invention is explained in more detail with reference to an exemplary embodiment with the attached drawings, in which.

DETAILED DESCRIPTION

Figure 1:
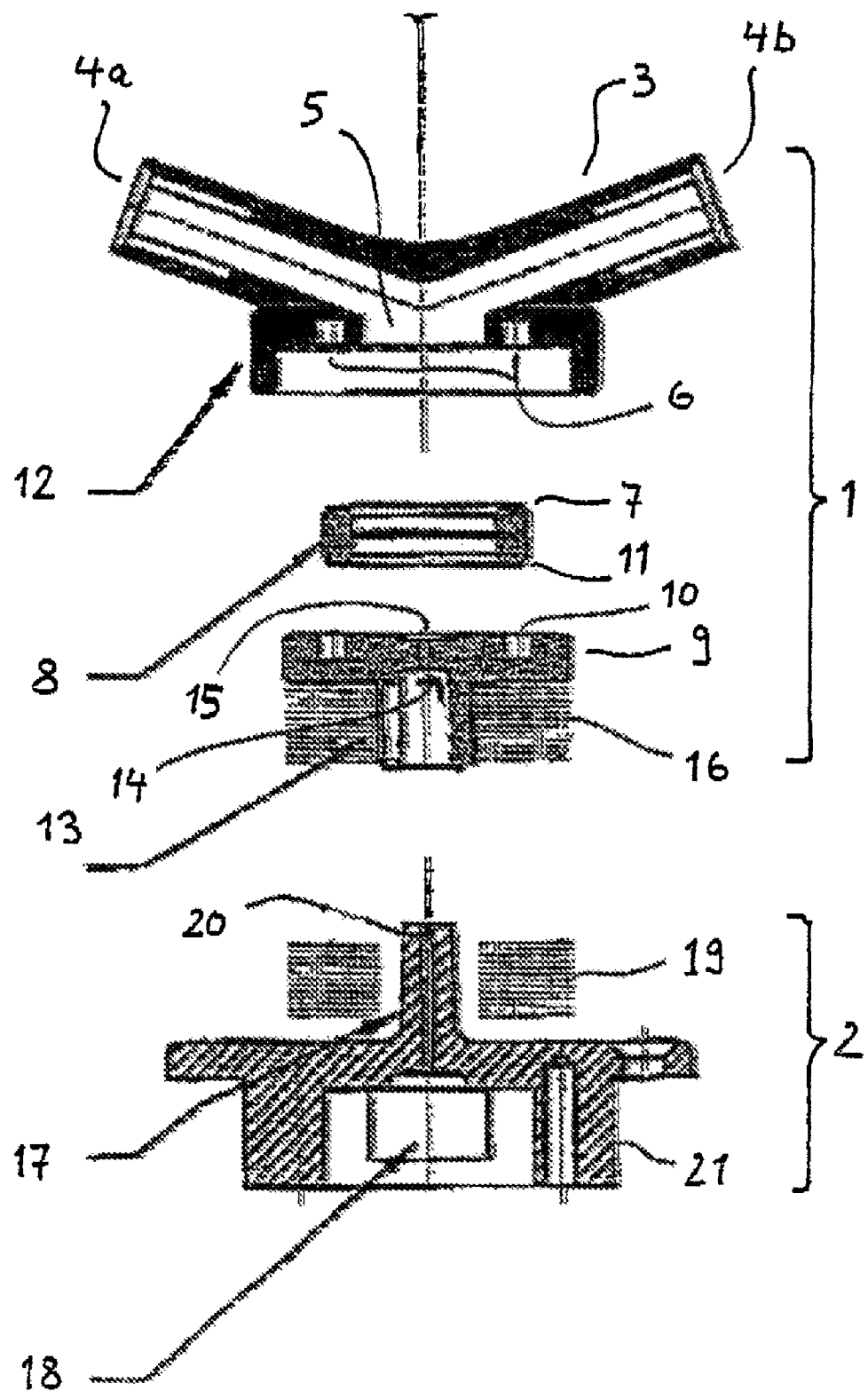
FIG. 1 shows an exploded view of a connecting element and associated pressure transducer in cross section.

FIG. 1 shows an exploded view of a connecting element 1 and of a pressure transducer 2 in cross section. The connecting element 1 has a housing 3 having a first and a second fluid line connection 4a, 4b, to which blood tubes of a dialysis or hemodialysis apparatus can be connected. Incorporated in the center of the housing is a measuring chamber 5, which is connected to the fluid line connections 4a, 4b. Arranged adjacent to the measuring chamber 5 is an encircling groove 6, into which a likewise encircling sealing ring 7 of a diaphragm 8 can be inserted in such a way that the diaphragm 8 seals the measuring chamber 5 toward the outside and sits in the diaphragm 8 securely and with restrained surface on the measuring chamber 5.

Furthermore, the connecting element 1 has a connecting section 9, which likewise has an encircling groove 10 for accommodating a corresponding sealing ring 11 of the diaphragm 8. This ensures that the air volume between diaphragm 8 and pressure transducer 2 is limited and no air can escape laterally through the diaphragm 8 to the outside.

The connecting section 9 is mounted with interposed diaphragm 8 onto the housing 3 and is firmly connected to the latter, for example by adhesive bonding or welding. To this end, a collar 12, for example, is provided on the housing 3, and this collar 12 overlaps the connecting section 9 and can be used for the airtight connection of the connecting section 9 and the housing 3.

The connecting section 9 has a tubular connection 13, which extends away downward in the fitted-together state of the housing 3 and the bearing surface of the connecting section 9. To define the air volume between diaphragm 8 and pressure transducer 2, a relatively small bore 13 is incorporated in the bearing surface of the connecting section 9. The air volume should be as small as possible in order to permit a sufficiently accurate measurement.

Also indicated is the fact that a hollow 15 is incorporated adjacent to the diaphragm 8 in the bearing surface of the connecting section 9, into which hollow 15 the diaphragm 8 can be put when there is a positive pressure in the measuring chamber 5 relative to the atmosphere. The air volume between diaphragm 8 and pressure transducer 2 can be compressed in this way and measurement of positive pressures can be made possible.

The tubular connection 13 has a locking element 16 (indicated by broken lines) in order to mount the connecting element 1 onto the pressure transducer 2 in a simple, reliable and airtight manner. To this end, a corresponding connecting tube 17 of the pressure transducer 2 extends upward away from a pressure sensor 18. Adjacent to the connecting tube 17, a locking element 19 is likewise provided on the pressure transducer 2 and interacts with the locking element 16 of the connecting element 3.

An air volume that is as small as possible is ensured between pressure sensor 18 and diaphragm 8 by a relatively small bore 20 in the connecting tube 17 when the connecting element 3 is mounted onto the pressure transducer 2.

The locking element 16 can be designed, for example, as a screw cap with screw thread or as a bayonet catch in a manner known per se for other applications. In this case, it is advantageous if a lever projects transversely to the longitudinal axis of the tubular connection 13, by means of which lever the locking element can be rotated by the angle required for locking. The locking element 16 is preferably designed in such a way that a rotation of at most 90° and preferably of about 45° is required for locking and unlocking.

Figure 2:
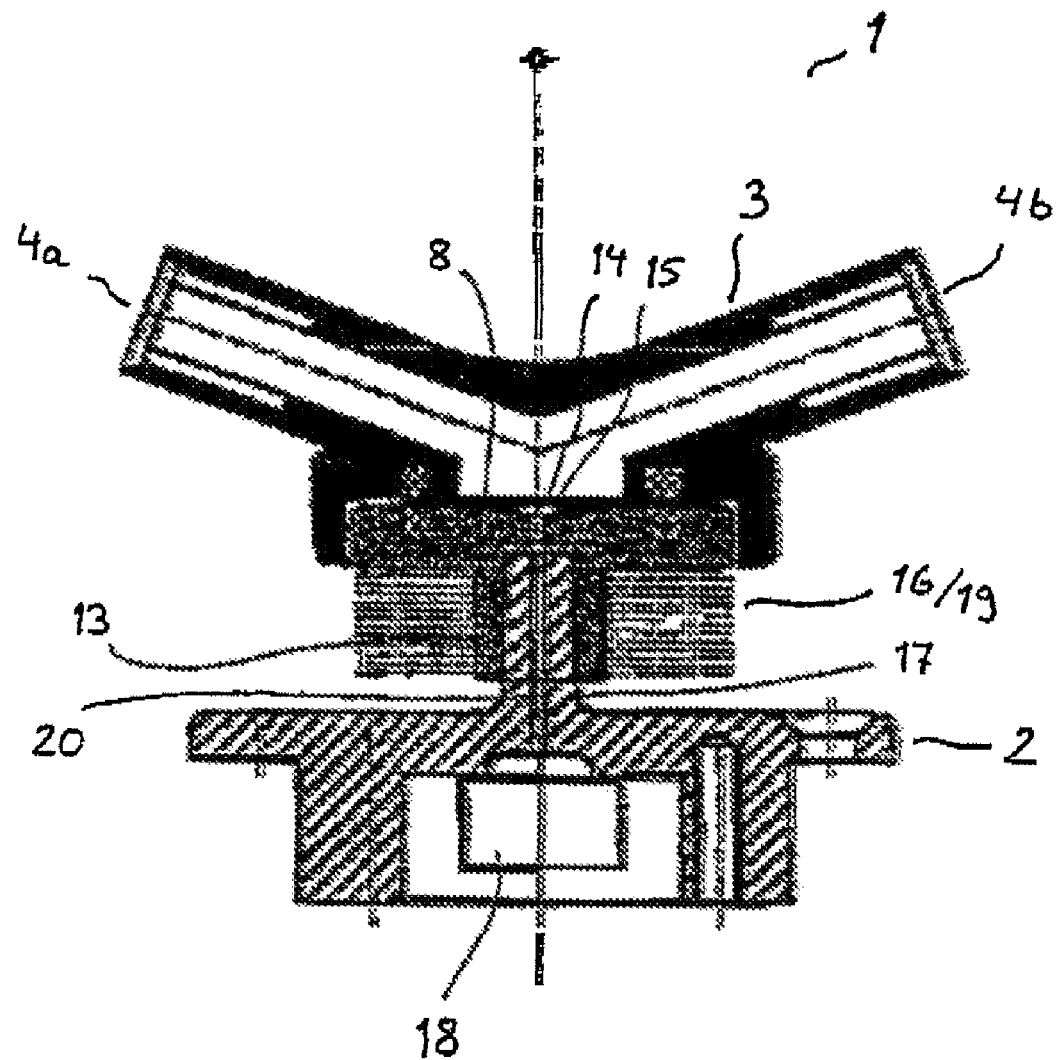
FIG. 2 shows a cross-sectional view of a connecting element mounted onto a pressure transducer.

FIG. 2 shows a cross-sectional view of the connecting element 1 from FIG. 1 which is mounted onto the pressure transducer 2. Here, the locking element 16 of the connecting element 1 engages in the locking element 19, integrally formed on the pressure transducer housing 21, of the pressure transducer 2 in such a way that the connecting element 1 sits firmly and tightly on the pressure transducer 2.

It can also be seen that the bores 15 and 20 are in alignment with one another and communicate with the pressure sensor 18 and the hollow 15 below the diaphragm 8. In this way, a small defined air volume is provided between diaphragm 8 and pressure sensor 18.

The invention claimed is:

1. A connecting element for the releasable sealed connection of a fluid line system to a pressure transducer for detecting positive and negative pressures of a fluid located in the connecting element comprising:
 a housing,
 at least one fluid line connection to the housing,
 a measuring chamber in the housing which measuring chamber communicates with the fluid line connection,
 a diaphragm adjacent to the measuring chamber, which diaphragm is tightly connected to the housing for sealing the measuring chamber, and
 a connecting section on the housing for a repeatedly releasable connection of the connecting element to the pressure transducer, wherein the connecting section has a tubular connection pointing away from the housing and for slipping onto or into a corresponding connecting tube of the pressure transducer, and at least one locking element for the repeatedly releasable connection of the connecting element to the pressure transducer, the tubular connection communicating with the diaphragm and being designed for the airtight connection of the connecting element to the pressure transducer.

2. The connecting element as claimed in claim 1, wherein the locking element is designed as a screw cap with screw thread.

3. The connecting element as claimed in claim 2, wherein the locking element is designed as a Luer-lock connection.

4. The connecting element as claimed in claim 1, wherein the locking element is designed as a bayonet catch element.

5. The connecting element as claimed in claim 4, wherein the tubular connection has at least one longitudinal slot extending from a free end in the direction of diaphragm and a transverse slot projecting at right angles from an end of the longitudinal slot.

6. The connecting element as claimed in claim 4, wherein the tubular connection has at least one button-like prominence for inserting into a bayonet catch slot of the pressure transducer.

7. The connecting element as claimed in claim 1, wherein the locking element has a sleeve part rotatable relative to the tubular connection and having a lever which projects away from the sleeve part and is intended for locking the connecting element on the pressure transducer.

8. The connecting element as claimed in claim 1, further comprising a hollow in the housing adjacent to the diaphragm and diametrically opposite the measuring chamber.

9. The connecting element as claimed in claim 1, wherein the connecting section is mounted onto the housing in a position directly adjacent to the diaphragm and is connected to the housing in an airtight manner in such a way that air pressure is transmitted exclusively from the diaphragm via the tubular connection to the pressure transducer.

10. The connecting element as claimed in claim 1, wherein the diaphragm has an encircling sealing ring on one side and the housing and encircling grooves for accommodating the sealing ring of the diaphragm and for the airtight and fluid-tight connection of the housing to the diaphragm.

11. The connecting element as claimed in claim 1, wherein the diaphragm has a respective encircling sealing ring on both sides, and the housing and the connecting section have encircling grooves for accommodating corresponding sealing rings of the diaphragm and for the airtight and fluid-tight connection between the housing, the diaphragm and the connecting section.

12. The connecting element as claimed in claim 1, wherein the housing, the diaphragm and the connecting section are adhesively bonded or welded to one another.

13. A pressure transducer for measuring the pressure of a measuring chamber, closed off with a diaphragm, of a separate connecting element, which can be connected to the pressure transducer in a releasable and sealed manner, comprising:
 a pressure transducer housing,
 a pressure sensor in the pressure transducer housing, and
 a connecting region, for the repeatedly releasable fastening of a connecting element to the pressure transducer housing, in such a way that the connecting element is connected to the pressure transducer in an airtight manner and there is an air volume, sealed off relative to the atmosphere, between the diaphragm and the pressure sensor, such that a pressure of the diaphragm acts via the air volume on the pressure sensor,
 wherein the connecting region is a connecting tube for accommodating a tubular connection of the connecting element and has at least one locking element for a repeatedly releasable connection of the tubular connection of the connecting element to the connecting region.

14. The pressure transducer as claimed in claim 13, wherein the locking element is arranged on the outer circumference of the connecting tube in order to accommodate tubular connection, mounted onto the connecting tube, of the connecting element, and the interior space of the connecting tube defines the air volume.

15. The pressure transducer as claimed in claim 13, wherein the connecting tube is provided for accommodating the tubular connection of the connecting element in the interior space of the connecting tube, the interior space of the tubular connection defining the air volume.

16. The pressure transducer as claimed in claim 13, wherein the connecting tube has a screw cap or a bayonet catch.

17. The connecting element as claimed in claim 1, wherein said tubular connection includes a connecting tube having a small bore extending from the connection area for the diaphragm to the pressure transducer, so that the air volume between the diaphragm and the pressure transducer is defined by the bore.

* * * * *